US008383025B2

(12) United States Patent
Li et al.

(10) Patent No.: US 8,383,025 B2
(45) Date of Patent: Feb. 26, 2013

(54) METHOD OF MANUFACTURING MICRO PATTERNED DEVICE AND DEVICE OBTAINED BY THE METHOD

(75) Inventors: Changming Li, Singapore (SG); Ling Yu, Singapore (SG)

(73) Assignee: Nanyang Technological University, Singapore (SG)

( * ) Notice: Subject to any disclaimer, the term of this patent is extended or adjusted under 35 U.S.C. 154(b) by 40 days.

(21) Appl. No.: 12/783,476

(22) Filed: May 19, 2010

(65) Prior Publication Data
US 2010/0323924 A1 Dec. 23, 2010

Related U.S. Application Data

(60) Provisional application No. 61/296,592, filed on Jan. 20, 2010, provisional application No. 61/179,542, filed on May 19, 2009.

(51) Int. Cl.
*B32B 37/00* (2006.01)
(52) U.S. Cl. .......................... 264/134; 264/496; 156/500
(58) Field of Classification Search .................. 264/219, 264/134, 496; 438/378
See application file for complete search history.

(56) References Cited

U.S. PATENT DOCUMENTS

| | | | | |
|---|---|---|---|---|
| 6,063,589 | A | 5/2000 | Kellogg et al. .................. | 435/24 |
| 6,479,239 | B1 | 11/2002 | Anderson et al. .................. | 435/6 |
| 6,527,432 | B2 | 3/2003 | Kellogg et al. ............. | 366/182.1 |
| 6,716,823 | B1 | 4/2004 | Tang et al. ....................... | 514/44 |
| 2006/0131784 | A1* | 6/2006 | Sugimoto ..................... | 264/219 |

FOREIGN PATENT DOCUMENTS
WO    2005/095262    10/2005

OTHER PUBLICATIONS

Ajikumar et al., "Carboxyl-Terminated Dendrimer-Coated Bioactive Interface for Protein Microarray: High-Sensitivity Detection of Antigen in Complex Biological Samples" Langmuir 23: 5670-5677, 2007.
Bai et al., "Surface Modification for Enhancing Antibody Binding on Polymer-Based Microfluidic Device for Enzyme-Linked Immunosorbent Assay" Langmuir 22: 9458-9467, 2006.
Barbani et al., "Bioartificial materials based on blends of dextran and poly(vinyl alcohol-*co*-acrylic acid)" European Polymer Journal 41: 3004-3010, 2005.
Berdichevsky et al., "UV/ozone modification of poly(dimethylsiloxane) microfluidic channels" Sensors and Actuators B 97: 402-408, 2004.
Bodas et al., "Formation of more stable hydrophilic surfaces of PDMS by plasma and chemical treatments" Microelectronic Engineering 83: 1277-1279, 2006.
Boone et al., "Plastic Advances Microfluidic Devices: The devices debuted in silicon and glass, but, plastic fabrication may make them hugely successful in biotechnology application" Analytic Chemistry 74(3): 78A-86A, Feb. 1, 2002.
Brogan et al., "Influence of Surfactants and Antibody Immobilization Strategy on Reducing Nonspecific Protein Interactions for Molecular Recognition Force Microscopy" Langmuir 20: 9729-9735, 2004.
Chan-Park et al., "Fabrication of High Aspect Ratio Poly(ethylene glycol)-Containing Microstructures by UV Embossing" Langmuir 19: 4371-4380, 2003.
Chiem et al., "Microchip systems for immunoassay: an integrated immunoreactor with electrophoretic separation for serum theophylline determination" Clinical Chemistry 44(3): 591-598, 1998.
Chu et al., "Plasma polymerized epoxide functional surfaces for DNA probe immobilization" Biosensors and Bioelectronics 24: 118-122, 2008.
Davidsson et al., "Microfluidic biosensing systems Part I. Development and optimization of enzymatic chemiluminescent µ-biosensors based on silicon microchips" Lab Chip 4: 481-487, 2004.
Decker, "Kinetic Study and New Applications of UV Radiation Curing" Macromol. Rapid Commun. 23(18): 1067-1093, 2002.
Deng et al., "Transport at the Air/Water Interface is the Reason for Rings in Protein Microarrays" J. Am. Chem. Soc. 128: 2768-2769, 2006.
Dong et al., "Screen-printed microfluidic device for electrochemical immunoassay" Lab Chip 7: 1752-1758, 2007.
Efimenko et al., "Surface Modification of Sylgard-184 Poly(dimethyl siloxane) Networks by Ultraviolet and Ultraviolet/Ozone Treatment" Journal of Colloid and Interface Science 254: 306-315, 2002.
Eteshola et al., "Development and characterization of an ELISA assay in PDMS microfluidic channels" Sensors and Actuators B 72: 129-133, 2001.
Fan et al., "Characterization of Cellulose Aldehyde Using Fourier Transform Infrared Spectroscopy" Journal of Applied Polymer Science 82: 1195-1202, 2001.
Hang et al., "Frequency dependent and surface characterization of DNA immobilization and hybridization" Biosensors and Bioelectronics 19: 1537-1548, 2004.
He et al., "Novel Immunofluorescence Assay Using Recombinant Nucleocapsid-Spike Fusion Protein as Antigen To Detect Antibodies against Severe Acute Respiratory Syndrome Coronavirus" Clinical and Diagnostic Laboratory Immunology 12(2): 321-328, Feb. 2005.
Herrmann et al., "Enzymatically-generated fluorescent detection in micro-channels with internal magnetic mixing for the development of parallel microfluidic ELISA" Lab Chip 6: 555-560, 2006.
Hsiao et al., "Aminopropyltriethoxysilane (APTES)-functionalized nanoporous polymeric gratings: fabrication and application in biosensing" J. Mater. Chem. 17: 4896-4901, 2007.
Huang et al., "Serum Interleukin-5 Measurements for Monitoring Acute Asthma in Children" Journal of Asthma 42: 297-300, 2005.
Jin et al., "A fast low-temperature micromolding process for hydrophilic microfluidic devices using UV-curable acrylated hyperbranched polymers" J. Micromech. Microeng. 17: 1147-1153, 2007.

(Continued)

*Primary Examiner* — Natalia Levkovich
(74) *Attorney, Agent, or Firm* — Seed IP Law Group PLLC

(57) ABSTRACT

The present invention refers to a method of manufacturing a micro patterned device. The method can comprise or consist of applying a light curable epoxy resin to a mold to obtain a curable resin filled mold. In a further step a polymeric film or an epoxy resin-coated glass is applied over the curable resin filled mold. Subsequently, the curable resin filled mold to which the polymeric film or the epoxy resin-coated glass is applied is irradiated to cure the resin. In another aspect the present invention refers to a micro patterned device obtained by a method described herein.

16 Claims, 8 Drawing Sheets

OTHER PUBLICATIONS

Khademhosseini et al., "A Soft Lithographic Approach To Fabricate Patterned Microfluidic Channels" Anal. Chem. 76(13): 3675-3681, 2004.
Kim et al., "Magnetic force-based multiplexed immunoassay using superparamagnetic nanoparticles in microfluidic channel" Lab Chip 5: 657-664, 2005.
Lai et al., "Viral hepatitis B" Lancet 362: 2089-2094, Dec. 20-27, 2003.
Larsson et al., "Photografted Poly(ethylene glycol) Matrix for Affinity Interaction Studies" Biomacromolecules 8: 287-295, 2007.
Larsson et al., "UV-Patterned Poly(ethylene glycol) Matrix for Microarray Applications" Biomacromolecules 8: 3511-3518, 2007.
Liu et al., "Optimization of printing buffer for protein microarrays based on aldehyde-modified glass slides" Frontiers in Bioscience 12: 3768-3773, May 1, 2007.
Liu et al., "Dual fluorescence/contactless conductivity detection for microfluidic chip" Analytica Chimica Acta 621: 171-177, 2008.
Liu et al., "Home-made capillary array electrophoresis for high-throughput amino acid analysis" Analytica Chimica Acta 622: 169-174, 2008.
Liu et al., "High performance protein microarrays based on glycidyl methacrylate-modified polyethylene terephthalate plastic substrate" Talanta 77: 1165-1171, 2009.
Luo et al., "PDMS microfludic device for optical detection of protein immunoassay using gold nanoparticles" Lab Chip 5: 726-729, 2005.
Manz et al., "Miniaturized Total Chemical Analysis Systems: a Novel Concept for Chemical Sensing" Sensors and Actuators B1: 244-248, 1990.
MacBeath et al., "Printing Proteins as Microarrays for High-Throughput Function Determination" Science 289: 1760-1763, Sep. 8, 2000.
McDonald et al., "Fabrication of microfluidic systems in poly(dimethylsiloxane)" Electrophoresis 21: 27-40, 2000.
Moorthy et al., "Microfluidic tectonics platform: A colorimetric disposable botulinum toxin enzyme-linked immunosorbent assay system" Electrophoresis 25: 1705-1713, 2004.
Nam et al., "Epoxy-silane linking of biomolecules is simple and effective for patterning neuronal cultures" Biosensors and Bioelectronics 22: 589-597, 2006.
Ombelli et al., "Dextran Grafted Silicon Substrates: Preparation, Characterization And Biomedical Applications" Mat. Res. Soc. Symp. Proc. 774: 93-98, 2003.
Pamme et al., "Counting and sizing of particles and particle agglomerates in a microfluidic device using laser light scattering: application to a particle-enhanced immunoassay" Lab Chip 3: 187-192, 2003.
Phillips et al., "Microfluidic Immunoassay for Bacterial Toxins with Supported Phospholipid Bilayer Membranes on Poly(dimethylsiloxane)" Anal. Chem. 77(1): 327-334, 2005.
Pittock et al., "Neuromyelitis Optica and Non-Organ-Specific Autoimmunity" Arch. Neurol. 65(1): 78-83, 2008.
Qin et al., "Microfabrication, Microstructures and Microsystems" Topics in Current Chemistry 194: 1-20, 1998.
Ressine et al., "Macro-/Nanoporous Silicon as a Support for High-Performance Protein Microarrays" Anal. Chem. 75(24): 6968-6974, 2003.
Rodella et al., "Quantitative analysis of HBsAg IgM anti-HBc and anti-HBc avidity in acute and chronic hepatitis B" Journal of Clinical Virology 37: 206-212, 2006.
Sales et al., "The incorporation of propane-1,3-diamine into silylant epoxide group through homogeneous and heterogeneous routes" Polyhedron 21: 2647-2651, 2002.
Sato et al., "Determination of Carcinoembryonic Antigen in Human Sera by Integrated Bead-Bed Immunoasay in a Microchip for Cancer Diagnosis" Anal. Chem. 73(6): 1213-1218, 2001.
Takatsu et al., "T Cell-Replacing Factor (TRG)/Interleukin 5 (IL-5): Molecular and Functional Properties" Immunological Reviews 102: 107-135, 1988.
Toepke et al., "PDMS adsorption of small molecules and consequences in microfluidic applications" Lab Chip 6: 1484-1486, 2006.
Wise et al., "Microfabrication Techniques for Integrated Sensors and Microsystems" Science 254: 1335-1342, 1991.
Wolter et al., "Preparation and Characterization of Functional Poly-(ethylene glycol) Surfaces for the Use of Antibody Microarrays" Anal. Chem. 79(12): 4529-4537, 2007.
Wu et al., "Grafting epoxy-modified hydrophilic polymers onto poly(dimethylsiloxane) microfluidic chip to resist nonspecific protein adsorption" Lab Chip 6: 942-947, 2006.
Wu et al., "Development of Indirect Enzyme-linked Immunosorbent Assay with Nucleoprotein as Antigen for Detection and Quantification of Antibodies against Avian Influenza Virus" Veterinary Research Communications 31: 631-641, 2007.
Yakovleva et al., "Microfluidic enzyme immunosensors with immobilised protein A and G using chemiluminescence detection" Biosensors and Bioelectronics 19: 21-34, 2003.
Yang et al., "AFM and impedance spectroscopy characterization of the immobilization of antibodies on indium-tin oxide electrode through self-assembled monolayer of epoxysilane and their capture of *Escherichia coli* O157:H7" Biosensors and Bioelectronics 20: 1407-1416, 2005.
Yu et al., "Efficient Probe Immobilization on Poly(Dimethylsiloxane) for Sensitive Detection of Proteins" Frontiers in Bioscience 10: 2848-2855, Sep. 1, 2005.
Yu et al., "Poly(vinyl alcohol) Functionalized Poly(dimethylsiloxane) Solid Surface for Immunoassay" Bioconjugate Chemistry 18(2): 281-284, Mar./Apr. 2007.
Zhang et al., "Capillary electrophoresis of proteins in dextran-coated columns" Electrophoresis 24: 115-120, 2003.
Zhang et al., "Fabrication of thin-film organic transistor on flexible substrate via ultraviolet transfer embossing" Applied Physics Letters 90: 243502-01-243502-03, 2007.
Zhou et al., "Protein microarrays on hybrid polymeric thin films prepared by self-assembly of polyelectrolytes for multiple-protein immunoassays" Proteomics 6: 1415-1426, 2006.

\* cited by examiner

METHOD OF MANUFACTURING MICRO PATTERNED DEVICE AND DEVICE OBTAINED BY THE METHOD

CROSS-REFERENCE TO RELATED APPLICATIONS

This application claims the benefit of priority of U.S. provisional application No. 61/179,542, filed May 19, 2009, and U.S. provisional application No. 61/296,592, filed Jan. 20, 2010, the contents of which are hereby incorporated by reference in their entireties for all purposes.

FIELD OF THE INVENTION

The present invention refers to the field of polymer chemistry, in particular to polymer chemistry for the manufacture of micro patterned devices.

BACKGROUND OF THE INVENTION

Advanced analytical techniques are towards micro-analyzers with advantages of small sample requirement, reduced assay time, low manufacturing cost, and portable flexibility. Up to date, immunoassay is still the main stream in the clinical diagnostic methods and is widely used in various selective and sensitive detections of small and large molecules through specific bindings of antibody and antigen. The research and development of immunoassay continues to fuel up by the high demand of the society for health care quality, food quality control, monitoring and biological security. With current progress in versatile, inexpensive, and reliable techniques for microfabrication and bio-interaction, antibody microarrays and microfluidic immunosensors, or their combinations bring about new generation of powerful analytical tools for important applications in proteomics, drug discovery and diagnostics.

Most of the early devices used for such methods were made using silicon and glass as the substrates, since their microfabrication including patterning, etching and bonding can directly borrow the matured technology from the semiconductor industry. As an economic alternative, polymer substrate was employed to fabricate the microfluidic device by simple molding instead of the expensive patterning process used in semiconductor industry. However, the surface properties of the polymer microdevices are varied due to diversity of the physical and chemical properties of the polymeric materials in use.

For example, microfluidic immunoassay devices have been made with for example with poly(dimethylsiloxane) (PDMS). PDMS as an economic alternative is one of the polymer substrates mostly used due to its high cast fidelity in a mold. However, its resin takes a long time (a number of hours) to cure, and the device has strong non-specific interference caused by its hydrophobic nature. Thus, surface modification is usually a must to improve protein probe attachment and eliminate non-specific adsorption. Additionally, the polymer microfluidic device so far needs a complicated manufacture process to fabricate its 3D patterned structure including master microfabrication, polymer structure molding and surface modification.

Thus, it is an object of the present invention to provide alternative fabrication methods for microdevices which can be used for example for chemical and/or biological assays and which require reduced surface modification for the binding of certain molecules.

SUMMARY OF THE INVENTION

The present invention refers to a method of manufacturing a micro patterned device. The method can comprise or consist of applying a light curable epoxy resin to a mold to obtain a curable resin filled mold. In a further step a polymeric film is coated over the curable resin filled mold. In one embodiment an epoxy resin coated glass is applied over the curable resin filled mold. Subsequently, the curable resin filled mold covered with the polymeric film or epoxy resin-coated glass slide is irradiated to cure the resin. In another aspect the present invention refers to a micro patterned device obtained by a method described herein.

BRIEF DESCRIPTION OF THE DRAWINGS

The invention will be better understood with reference to the detailed description when considered in conjunction with the non-limiting examples and the accompanying drawings, in which:

FIG. 3(B) illustrates the effects of glycerol and triton X-100 on signal intensity. G: glycerol, T: Triton X-100.

DETAILED DESCRIPTION OF THE PRESENT INVENTION

Figure 1A:
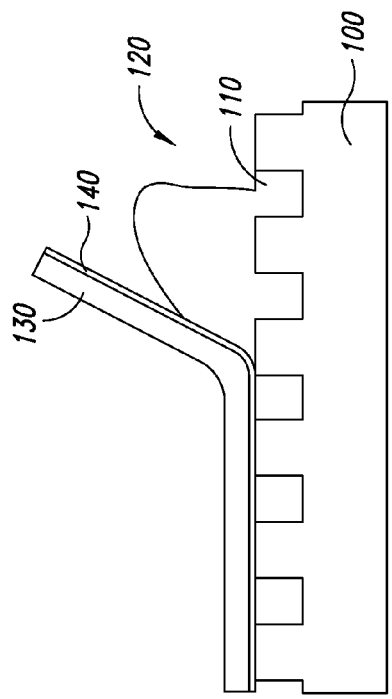
As shown in FIG. 1A, a mold (100) is filled with a light curable epoxy resin (110) to provide a filled mold (120). The filled mold (120) is coated with a polymeric film (130). The polymeric film (130) can be pre-coated and cured with a coating (140) that can be the epoxy resin mixture used to fill the mold or a resin mixture of different composition, as shown in FIG. 1B. After coating, as shown in FIG. 1C, the epoxy resin (110) is cured via irradiation with light that initiates curing (hardening) of the epoxy resin. After curing, as shown in FIG. 1D, the micro patterned newly formed device can be peeled off and be used for further applications, such as assembling to obtain a microfluidic device and/or immobilizing target molecules at the surface of the device for biological and/or chemical assays.

In a first aspect, the present invention refers to a method of manufacturing a micro patterned device. The method can comprise or consist of applying a light curable epoxy resin to a mold to obtain a curable resin filled mold. In a further step a polymeric film is coated over the curable resin filled mold. In one embodiment an epoxy resin coated glass is applied over the curable resin filled mold. Subsequently, the curable resin filled mold covered with the polymeric film or epoxy resin-coated glass slide is irradiated to cure the resin.

The method of the present invention provides a simple approach using an epoxy resin to directly fabricate a three dimensional structure while simultaneously introducing the epoxy group to efficiently immobilize target molecules, such as proteins at the surface of the micro patterned device fabricated with this method.

Applying the light curable epoxy resin to the mold can be carried out by pouring the non cured and liquid epoxy resin into the mold. A mold is a hollowed-out block that is filled with the liquid epoxy resin. The epoxy resin is cured (hardens) or sets inside the mold adopting its shape. A mold is opposite of a cast. The mold provides the pattern that resembles a negative of the micro patterned device, such as a microfluidic device to be formed by filling the light curable epoxy resin into the mold.

A "microfluidic device" refers to a device that can be used to control and manipulate fluids with volumes on the order of microliters, or nanoliters or picoliters. The devices themselves have dimensions in the millimeter and/or micrometer range. The dimensions can also be ranging from a few centimeter or millimeters (mm) down to micrometers (μm) and are also often referred to as microchip or Lab-on-a-chip.

The mold can be made of a material including, but not limited to poly(methyl methacrylate) (PMMA), acetonitrile-butadiene-styrene (ABS), polyethylene terephthalate (PET), poly-(dimethylsiloxane) (PDMS), polycarbonate, polyethylene, polystyrene, polyolefin, polypropylene, polyimide, and a polymeric organosilicon.

The polymeric organosilicon can include, but is not limited to poly(dimethyl siloxane) (PDMS) or poly(methyl hydrosiloxane) (PMHS). Methods for manufacturing molds are known in the art, such as photolithographic methods. The mold material composition can be adjusted to be flexible. A flexible mold allows easier separating of the hardened epoxy resin from the mold without damaging the micro patterned device formed in the mold.

The micro patterned device is made of a composition comprising an epoxy resin. An epoxy resin is a resin characterized by the presence of the epoxy group. The epoxy or epoxide group is usually present as a glycidyl ether, glycidyl amine, or as part of an aliphatic ring system. Epoxy adhesives are thermosetting resins which solidify by polymerisation and, once set, will soften but not melt on heating.

Micro patterned devices made of epoxy resins provide epoxy groups at their surface. Depending on the use of the micro patterned device the functional epoxy group can be used to immobilize target molecules at their surface such as through covalent binding. For example, an epoxy can react with nucleophiles in a ring-opening process. The reaction can take place with primary amines, sulfhydryls or hydroxyl groups, for example of proteins or other molecules to create secondary amines, thioether, or ether bonds, respectively. During the coupling process, ring opening forms a β-hydroxy group on the epoxy compound.

In one embodiment, the epoxy group can be further functionalized to be conjugated, such as by covalent bonding, to a reactive group. Such a reactive group can be an amino group, or a carboxylic acid group, or a hydroxyl group, or a thiol group for binding different kinds of target molecules.

Suitable epoxy resins which can be used herein include, but are not limited to commercially available epoxy resins. Such epoxy resins can include, but are not limited to polyhydric phenol polyether alcohols; glycidyl ethers of novolac resins, such as epoxylated phenol-formaldehyde novolac resin, glycidyl ethers of mononuclear di- and trihydric phenols; glycidyl ethers of bisphenols, such as diglycidyl ether of tetrabromobisphenol A; glycidyl ethers of polynuclear phenols; epoxy resin from diphenolic acid; glycidyl ethers of aliphatic polyols, such as chlorine-containing aliphatic diepoxy and polyepichlorohydrin; glycidyl esters such as aliphatic diacid glycidyl esters and epoxidized phenolphthalein; glycidyl epoxies containing nitrogen, such as glycidyl amides and amide-containing epoxies; glycidyl derivatives of cyanuric acid; glycidyl resins from melamines; glycidyl amines, such as triglycidyl ether amine of p-aminophenol and bis(2,3-epoxypropyl)methylpropylammonium p-toluenesulfonate; and glycidyl triazines; thioglycidyl resins, such as epoxidized bisulfide; silicon-glycidyl resins such as 1,4-bis[(2,3-epoxypropoxy)dimethylsilyl]; fluorine glycidyl resins; epoxy resins which are synthesized from monoepoxies other than epihalohydrins including epoxy resins from unsaturated monoepoxies, such as polyallyl glycidyl ether and glycidyl sorbate dimer; epoxy resins from monoepoxy alcohols; epoxy resins from monoepoxies by ester interchange; epoxy resins from glycidaldehyde; polyglycidyl compounds containing unsaturation, such as allyl-substituted diglycidyl ether of bisphenol A; epoxy resins which are synthesized from olefins and chloroacetyls, such as butadiene dioxide, vinylcyclohexene dioxide, epoxidized polybutadiene, and bis (2,3-epoxycyclopentyl)ether; epoxy-resin adducts of the above or mixtures of the aformentioned epoxy resins.

In one example, epoxy resins can include epoxy acrylates which include partially acrylated bisphenol-A epoxy resin or diacrylate esters of bishphenol derivatives. An example of a partially acrylated bisphenol-A epoxy resin includes EBECRYL 3605. EBECRYL 3605 oligomer is a partially acrylated bisphenol A epoxy resin containing both acrylate and epoxy functionality (see Formula I).

(FORMULA 1)

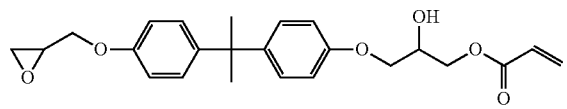

For example, the dual functionality of EBECRYL 3605 can react via any combination of ultraviolet light (UV) or electron beam (EB). In general, epoxy acrylates, such as epoxy di(meth)acrylate oligomers are available under trade designation "EBECRYL" (for example, "EBECRYL 230", "EBECRYL 3605", and "EBECRYL 8804") from UCB Radcure, Smyrna, Ga., and "CN" (for example, "CN 104") from Sartomer Co., Exton, Pa.

Light curing refers to hardening of a polymer material by cross-linking of polymer chains, brought about by light. Light used for the curing process can be used depending on the epoxy resin in the spectral range from about 10 nm to about 700 nm. Visible light curing takes place in a range from >400 nm to 700 nm. Curing with UV light is in a range from between about 10 nm to 400 nm. In one example, curing takes place at a wavelength of 100 to 200 nm. Curing takes place for a time of about a few seconds or minutes only. In one example, curing took place for about 5 seconds with a 400 W Hg lamp.

The epoxy resin used in the method of the present invention can be mixed with one or more photoinitiators. Such a photoinitiator is a chemical compound that decomposes into free radicals when exposed to light. The free radicals promote polymerization and thus hardening of the light curable expoxy resin. The photoinitiator(s) can be added to the epoxy resin in an amount of about 0.5% (w/w). In one embodiment, the concentration range for the photoinitiator is between about 0.2% to about 2.0% (w/w).

Examples of photoinitiators that can be used include, but are not limited to benzophenone, benzophenone/1-hydroxy-cyclohexylphenyl-ketone (1/1 ratio), 2,2-dimethoxy-2-phenylacetophenone (DMPA, Irgacure 651), 2-hydroxy-2-methyl-1-phenylpropanone, 1-hydroxy-cyclohexylphenyl-ketone, 2,4,6-trimethylbenzoyl diphenyl phosphine oxide, isopropyl thioxanthone (2- and 4-isomer mixture), 2-methyl-1-[4-(methylthio)phenyl]-2-morpholino-propan-1-one, 2-ethylhexyl-4-(dimethylamino)benzoate, ethyl-4-(dimethylamino)benzoate, acrylated benzophenone derivative, benzophenone derivative, acrylated amine synergist, copolymerizable amine synergist, acrylated amine synergist, or methyldiethanolamine. In one example 2,2-dimethoxy-2-phenylacetophenone (DMPA, Irgacure 651) has been used as photoinitiator.

The light curable epoxy resin can be mixed together with at least one solvent. The solvent can be used to adjust the viscosity of the epoxy resin. The solvent can be an acrylate. The term "acrylate" can include acrylate or methacrylate monomers. Additionally, the acrylates can include acids, esters, amides, and substituted derivatives thereof. Generally, acrylates are $C_1$-$C_8$ alkyl acrylates or methacrylates. Examples of such acrylates include butyl acrylate, hexyl acrylate, tert-butyl acrylate, methylmethacrylate, butylmethacrylate, hexylmethacrylate, isobutylmethacrylate, and isopropylmethacrylate.

Other acrylates that can be used herein are copolymers of ethylene and alkyl acrylates. Copolymers of ethylene and alkyl acrylates can include ethylene-methylacrylate polymer, ethylene-ethyl acrylate polymer, or ethylene-butyl acrylate polymer. Examples can include copolymers comprising ethylenes having alkyl acrylates with about 1 to 4 carbon atoms in the alkyl group.

In one embodiment, diacrylates, triacrylates, tetraacrylates and mixtures thereof can be used. Examples of diacrylates can include, but are not limited to ethylene glycol diacrylate, propylene glycol diacrylate, diethylene glycol diacrylate, dipropylene glycol diacrylate, triethylene glycol diacrylate, tripropylene glycol diacrylate, tertraethylene glycol diacrylate, tetrapropylene glycol diacrylate, polyethylene glycol diacrylate, dipropylene glycol diacrylate, polypropylene glycol diacrylate, ethoxylated bisphenol A diacrylate, bisphenol A diglycidyl ether diacrylate, resorcinol diglycidyl ether diacrylate, 1,3-propanediol diacrylate, 1,4-butanediol diacrylate, 1,5-pentanediol diacrylate, 1,6-hexanediol diacrylate, neopentyl glycol diacrylate, cyclohexane dimethanol diacrylate, ethoxylated neopentyl glycol diacrylate, propoxylated neopentyl glycoldiacrylate, ethoxylated cyclohexanedimethanol diacrylate, propoxylated cyclohexanedimethanol diacrylate, epoxy diacrylate, aryl urethane diacrylate, aliphatic urethane diacrylate, polyester diacrylate, and mixtures thereof.

Examples of triacrylates can include, but are not limited to trimethylol propane triacrylate, glycerol triacrylate, ethoxylated trimethylolpropane triacrylate, propoxylated trimethylolpropane triacrylate, tris (2-hydroxyethyl) isocyanuratetriacrylate, ethoxylated glycerol triacrylate, propoxylated glycerol triacrylate, pentaerythritol triacrylate, aryl urethane triacrylates, aliphatic urethane triacrylates, melamine triacrylates, epoxy novolac triacrylates, aliphatic epoxy triacrylate, polyester triacrylate, or mixtures thereof.

Examples of tetraacrylates can include, but are not limited to di-trimethylolpropane tetraacrylate, pentaerythritol tetraacrylate, ethoxylated pentaerythritol tetraacrylate, propoxylated pentaerythritol tetraacrylate, dipentaerythritol tetraacrylate, ethoxylated dipentaerythritol tetraacrylate, propoxylated dipentaerythritol tetraacrylate, aryl urethane tetraacrylates, aliphatic urethane tetraacrylates, polyester tetraacrylates, melamine tetraacrylates, epoxy novolac tetraacrylates, ore mixtures thereof.

Exemplary mixtures of diacrylate and triacrylates can include, but are not limited to mixtures of hexanediol diacrylate with pentaerythritol triacrylate, hexanediol diacrylate with trimethylolpropane triacrylate, diethyleneglycol diacrylate with pentaerythritol triacrylate, dipropylene glycol diacrylate with trimethylolpropane triacrylate, or diethyleneglycol diacrylate with trimethylolpropane triacrylate. In one embodiment a mixture of dipropylene glycol diacrylate with trimethylolpropane triacrylate has been used. For example, the mole ratio of epoxy acrylate to total solvent (such as acrylate solvent) can be between about 0.04 to 0.36.

In one embodiment, the epoxy resin can be liquefied, for example by heating, before addition of one or more photoinitiators and/or one or more solvents. The melting temperature of epoxy resins can be between about 50 to 150° C. For example, Ebecryl 3605 was liquefied at a temperature of about 60° C. for about half an hour. After addition of the one or more photoinitiator and/or one or more solvent the mixture can be incubated for a certain period of time. In one example an epoxy resin mixture including photoinitiator and solvent was incubated overnight.

Figure 1B:
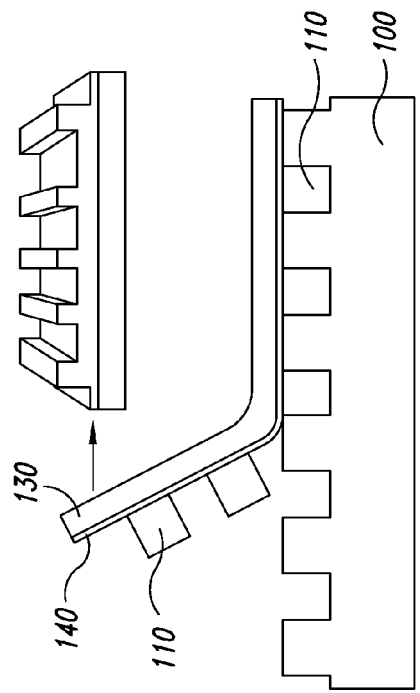
FIG. 1 illustrates the subject matter of the method referred to in the present invention.
Figure 1C:
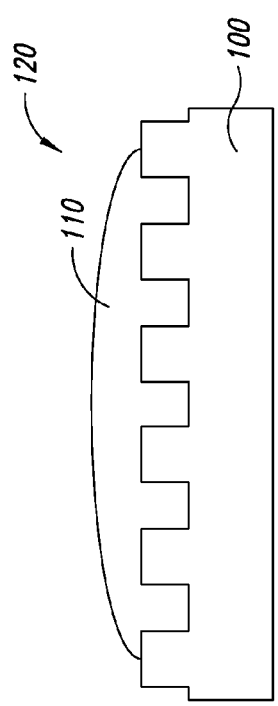

The polymeric film serves as a support structure or backing structure for the patterned microdevice formed in the mold. The polymeric film is coated over the filled mold to contact the epoxy resin filled in the mold. During curing, the polymer film connects to the curing polymer, which forms a permanent connection to the polymeric film. In one embodiment, as shown in FIGS. 1A-1B, the polymeric film (130) is coated on one side with a layer of the light curable resin (140) prior to coating the polymeric film over the curable resin filled mold (120). The polymeric film (130), which is coated on one side with the layer of the light curable resin (140), is then coated over the curable resin filled mold (120) with the side that was coated with a layer of the light curable resin (140). See, FIG. 1B. Excess acrylate group on the cured epoxy resin film can react with the acrylate group in the uncured resin by photoinitiator induced polymerization to form a covalent bond which is similar to the curing process of a liquid resin. The thickness of the coated epoxy resin layer can be in the range of between about 50 μm to about 1000 μm.

In another embodiment an epoxy resin-coated glass can be used instead of the epoxy resin-coated polymeric film. The glass can be coated with the same or a different epoxy resin as described herein. In that case the epoxy resin-coated glass is applied over the filled mold, such as by pressing it on the mold. The epoxy resin coated glass can be fabricated by spin coating a thin layer of epoxy resin (about 50 µm to about 1000 µm) on a glass slide. To improve the adhesion of epoxy resin on glass, the glass can be pretreated with acrylate silane to introduce acrylate group on glass surface to obtain an acrylate silane pre-treated glass slide.

The pre-formed layer of epoxy resin on the polymeric film can be made of the same or different epoxy resin material or mixture filled in the mold. The layer of epoxy resin on the polymeric film can be applied to the polymeric film via any method known in the art, such as spin coating or dropping. Spin coating can be carried out under an inert atmosphere, such as a nitrogen atmosphere. After applying the layer of epoxy resin on the polymeric film the epoxy resin is hardened. After hardening the thus formed layered structure of epoxy resin coated polymeric film is washed to remove any uncured or unpolymerized epoxy resin. Washing can be carried out with an alcohol, such as ethanol, and water. The same method can be used to cover the glass with an epoxy-resin layer.

The polymeric film can be made of the same or a different material than the mold. In one embodiment the mold is made of PMMA while the polymeric film is made of PET.

In one embodiment, coating of the polymeric film over the mold filled with epoxy resin can be carried out using laminating the polymeric film over the filled mold.

Furthermore, the epoxy resin can be filled into the mold to a level so that the epoxy resin exceeds the maximal height of the three-dimensional pattern of the mold to ensure that the mold is fully covered with the light curable epoxy resin. In other words the epoxy resin slightly overflows the empty space provided by the mold. This "overfilling" ensures in the subsequent coating that the polymeric film gets entirely in contact with the epoxy resin mixture.

Coating or laminating the polymeric film or the epoxy resin covered glass over the filled mold is followed by curing of the epoxy resin in the mold. After irradiation of the epoxy resin mixture for hardening, the micro patterned device formed can be removed from the mold, such as by peeling it off the mold as illustrated for example in FIG. 1(d). The whole manufacturing process of the micro patterned device as described herein can be carried out at ambient temperature. Ambient temperature is normally in a range of between about 15° to 35° C. or 20° C. to 25° C.

The micro patterned device described herein can be used to manufacture microfluidic devices. The mold can be formed to resemble microchannels, inlets and outlets of the microfluidic device. During or after curing further components of a microfluidic device can be incorporated, such as metallic inlet or outlet tubes, valves or any other components that might be used in a microfluidic device and which is not intended to be formed by the hardened epoxy resin.

Figure 1D:
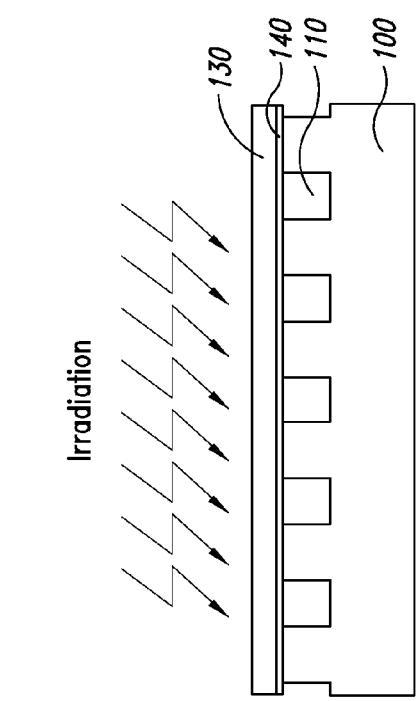
Figure 2A:
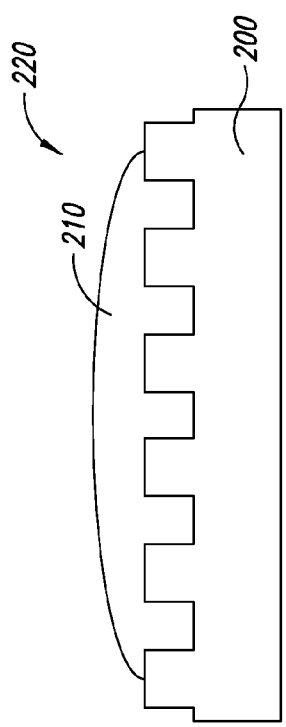
As shown in FIG. 2A, a polydimethylsiloxane (PDMS) mold (200) is filled with a light curable epoxy resin (210) to provide a filled mold (220). The polymeric film (230) is a polyethylene terephthalate (PET) which is pre-coated with an epoxy resin (240) and afterwards laminated over the filled mold (220), as shown in FIG. 2B. After the curing process is conducted under UV radiation, as shown in FIG. 2C, the mold (200) is carefully removed to obtain the micro patterned device, as shown in FIG. 2D. Thus, the UV curable epoxy resin could be used in a simple one-step fabrication of a microfluidic, e.g., ELISA device by UV embossing.
Figure 2B:
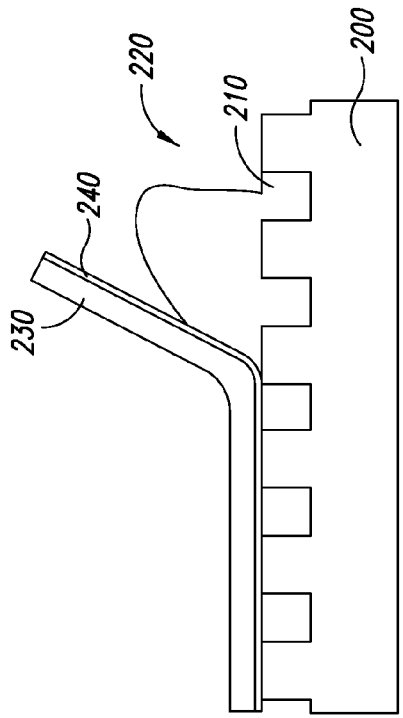
FIG. 2 illustrates a specific embodiment in which the light curable epoxy resin is an epoxy resin curable with UV light.
Figure 2C:
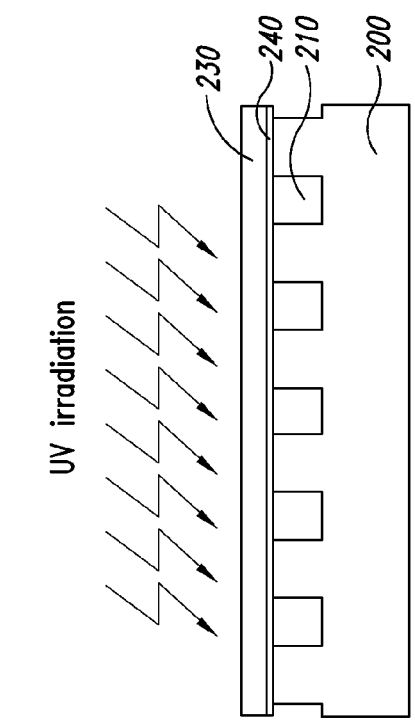
Figure 2D:
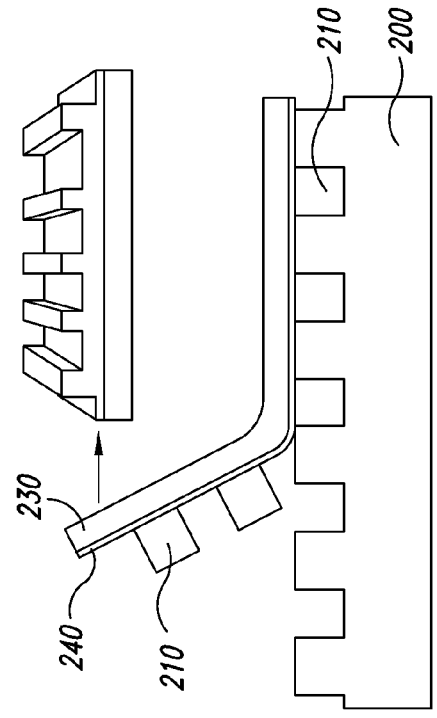

As illustrated for example in FIGS. 1(d) and 2(d), the formed three-dimensional structure formed can be covered by a further layer made of any material suitable to be used for microfluidic devices. For example, the finishing layer could be made of a transparent, such as glass or translucent material which allows observing the inside of the microfluidic device during use. In general, the material could be a silica based material, ceramic material or a polymeric material, such as a polymeric material already mentioned herein or another epoxy resin layer, or combinations thereof. A silica based material can be a glass. Examples of suitable glass materials can include, but are not limited to borosilicate glass, fused silica glass, and quartz. Examples of ceramic materials include, but are not limited to conductive metal oxides, such as ReO, TiO, ZnO, $CrO_2$, $V_2O_3$, and various forms of indium tin oxide, and conductive transition metal nitrides, such as titanium nitride, zirconium nitride, and chromium nitride.

The same glass materials can also be used for the epoxy resin covered glass which is applied as backing structure during the manufacturing process of the micro patterned device as described above.

The micro patterned device obtained with the method of the present invention can also be used to manufacture microchips which can be used for example for protein assays or nucleic acid assays. It can also be used for lab-on-chip systems for applications, for example, in screening assays.

The epoxy resin surface of the micro patterned or microfluidic device can be modified to carry out chemical or biological assays on it. The epoxy groups can be used to bind or immobilize target molecules at the surface of the micro patterned device.

A target molecule can be any molecule that is needed for any kind of chemical or biochemical assay that one wishes to carry out with a micro patterned or microfluidic device, such as an organic or inorganic molecule. Those target molecules are selected to be capable of binding to the epoxy group found on the oxidized polysaccharide immobilized at the surface of the microfluidic device either directly or after chemical modification of the epoxy group, such as amidation.

A target molecule can for example include, but is not limited to peptide, a polypeptide, a peptoid, an inorganic molecule, a small organic molecule, nucleotides, carbohydrate, or a protein. The concentration of the target molecule used depends only on the application and availability of target molecule.

Peptoids can have a much higher cell permeability than peptides (see e.g., Kwon, Y.-U., and Kodadek, (2007) T., *J. Am. Chem. Soc.* 129, 1508-1509). A peptide may be of synthetic origin or isolated from a natural source by methods well-known in the art. The natural source may be mammalian, such as human, blood, semen, or tissue. A peptide or polypeptide may for instance be synthesized using an automated polypeptide synthesizer. Illustrative examples of polypeptides are an antibody, a fragment thereof and a proteinaceous binding molecule with antibody-like functions. In one embodiment, an antiobody can be directed against an interleukin, such as IL-5, or a surface antigen of hepatitis B-virus, such as HBsAg. Examples of (recombinant) antibody fragments are Fab fragments, Fv fragments, single-chain Fv fragments (scFv), diabodies or domain antibodies (Holt, L. J., et al., (2003) *Trends Biotechnol.*, 21, 11, 484-490). An example of a proteinaceous binding molecule with antibody-like functions is a mutein based on a polypeptide of the lipocalin family (WO 03/029462, Beste et al., (1999) *Proc. Natl. Acad. Sci. U.S.A.,* 96, 1898-1903). Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies (see WO 96/23879), proteins based on the ankyrin scaffold (Mosavi, L. K., et al., (2004) *Protein Science* 13, 6, 1435-1448) or crystalline scaffold (WO 01/04144) the proteins described in Skerra, (2000) *J. Mol. Recognit.* 13, 167-187, AdNectins, tetranectins, and avimers. Avimers contain so called A-domains that occur as strings of multiple domains in several cell surface receptors (Silverman, J., et al., (2005) *Nature Biotechnology* 23, 1556-1561). Adnectins, derived from a domain of human fibronectin, contain three loops that can be engineered for immunoglobulin-like binding to targets (Gill, D. S. & Damle, N. K., (2006) *Current Opinion in Biotechnology* 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the α-carbon atom. Peptoids are typically resistant to proteases and other modifying enzymes and can have a much higher cell permeability than peptides (see e.g., Kwon, Y.-U., and Kodadek, T., (2007) *J. Am. Chem. Soc.* 129, 1508-1509). Where desired, a modifying agent may be used that further increases the affinity of the respective moiety for any or a certain form, class etc. of target matter.

In one embodiment, the protein which can be immobilized at the surface of the micro patterned or microfluidic device via the epoxy group can be an enzyme, an antibody, an antigen, a cytokine. Such proteins can be proteins related to various diseases or cell signaling pathways.

In another embodiment, it is also possible to add further blocking agents to the surface of the micro patterned or microfluidic device before binding of the target molecule via the modified or unmodified epoxy group. Such blocking agents are known in the art and can include, but are not limited to bovine serum albumin (BSA), skimmed milk, goat serum, rabbit serum or casein. Such blocking agents are for example often used in immunoassays.

The method described herein provides a simple and fast method of manufacturing large amounts of micro patterned devices which can be used for the manufacture of microfluidic devices. For example, the micro patterned devices can be used for different analytical or diagnostical methods, such as an enzyme-linked immunosorbent assay (ELISA), a fluorescent immunoassay, a chemiluminescent immunoassay, or an electrochemical immunoassay.

An example of a microfluidic device which can be manufactured with the method described herein is a microchip as referred to in WO 05/095262 A1. Such a microchip comprises a substrate, an inlet channel in the substrate, an outlet channel in the substrate for guiding fluid below a fluid level, a plurality of test channels in the substrate for guiding fluid flow from the inlet channel to the outlet channel, each one of the test channels having an inlet for fluid communication with the inlet channel and an outlet channel for fluid communication with the outlet channel, the inlet elevated from the outlet for inhibiting back flow through the inlet, the outlet elevated from the fluid level for inhibiting back flow through the outlet; and one test site in each one of the test channels for detection of at least one of a specific molecule and a molecular interaction at the test site.

Each one of the channels can have a substantially flat bottom, the bottom of the inlet channel elevated from bottoms of the test channels, the bottoms of the test channels elevated from the bottom of the outlet channel. In one embodiment, the at least one of the test channels comprises a well for holding fluid therein.

In another embodiment, the inlet and outlet channels are adapted to allow a liquid to flow at a greater rate in said outlet channel than in said inlet channel. Also, each one of said test sites comprises a surface suitable for immobilizing specific molecules thereon.

The microchip can further comprise probe molecules immobilized at each one of said test sites, said probe molecules having specific affinity to selected target molecules. Different probe molecules can be immobilized at different ones of said test sites for detecting different target molecules. The microchip can further comprise a plurality of electrodes, one of said electrodes at each one of said test sites.

In one embodiment, at least one of said test channels comprises a narrowed section proximate said test site in said at least one test channel for guiding fluid towards said test site. The plurality of electrodes can be first electrodes, said microchip can further comprise a plurality of second electrodes, one of said second electrodes in each one of said test channels.

In another embodiment, the first electrodes can be interconnected and said second electrodes can be interconnected, such that each pair of said electrodes in each one of said test channels is uniquely addressable.

The microchip can comprise probe molecules immobilized proximate said first electrodes. The test channels can extend substantially in parallel.

The microchip can further comprise a dilution channel formed in said substrate, said dilution channel in fluid communication with said inlet channel and having a first inlet for reception of a first fluid and at least one second inlet for reception of a second fluid to dilute said first fluid. The at least one second inlet can comprise a plurality of second inlets. The substrate can be a polymeric substrate as described herein. The substrate can comprise polydimethylsiloxane (PDMS).

In the experimental section it is described that a microfluidic device obtained by a method described herein was used for carrying out an ELISA with specific proteins immobilized at the surface of the microfluidic device. The fabricated ELISA device demonstrated a detection limit of 100 pg mL$^{-1}$ and a dynamic range of 4 orders of magnitude in serum samples, which is even better than that measured in PBS with microfluidic devices made by more complicated fabrication processes. Devices fabricated with the method described herein can also be used to colorimetrically detect proteins via the naked eye for immunoassay applications. In an epoxy based protein microarray carried out with an microarray manufactured with a method described herein, a wide dynamic range of 6 orders of magnitude and a sensitivity limit of 10 pg mL$^{-1}$ was demonstrated. This can be partly ascribed to the epoxy groups for high efficient protein covalent attachment.

This cost inexpensive, fast and simple approach for fabrication of a sensitive microfluidic device and protein microarray described herein are only a few examples which allow for broad applications in both biomedical science and clinical diagnosis. It also provides a platform for portable micro patterned devices, such as microfluidic ELISA devices which allow result examination via the naked eye without further use of complicated optical apparatuses. It can also be used for point-of-care and/or high throughput screening of infections diseases.

For example, the micro patterned devices can be used for applications for the diagnosis and detection of tuberculosis diseases, or sexually transmitted diseases (STDs), such as trichomoniasis and syphilis.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Chemicals and Reagents

Trimethylolpropane tricarylate (TMPTA, SR-351), dipropylene glycol diacrylate (DPGD, SR-508) were supplied by Satomer, USA. Ebecryl 3605™ is a partially acrylated bisphenol A epoxy resin and was purchased from UCB SA, Belgium. 2,2-dimethoxy-2-phenylacetophenone (Irgacure 651) was purchased by Ciba Specialty Chemicals, Switzerland. Goat IgG, rabbit IgG, anti-rabbit IgG, Cy3-labeled anti-goat IgG, HRP-labeled anti-goat IgG, HRP-labeled anti-rabbit IgG, human serum, phosphate buffered saline (PBS, 0.01M pH 7.4) and tris buffered saline (TBS, 0.01M pH 8.0) containing 0.05% detergent Tween 20 were obtained from Sigma-Aldrich, USA. Human recombinant IL-5 and two anti-IL-5 monoclonal antibodies were kindly provided by BD, USA. Blocker™ casein in PBS (pH 7.4) was purchased from Pierce, Germany. Sodium metaperiodate and 3,3__,5,5_-tetramethyl benzidine, TMB, (1.25 mM TMB, 2.21 mM H2O2, pH 3.1) were purchased from Merck KGaA, Germany. Sylgard 184 PDMS pre-polymer and the curing agent were purchased from Dow Corning, USA. ARFlow® 90128 film (5 mil), a hydrophilic heat-sealed adhesive tape was obtained from Adhesives Research Inc. Singapore. The deionized (DI) water used in all experiments was produced by Q-Grad® 1, from Millipore Corporation, USA. All other used chemicals were of analytical grades and obtained from common commercial supplies.

Fabrication of Epoxy Resin Film on PET Substrate

TMPTA and DPGD were used as the solvents to adjust the viscosity of the resin and also to effectively dissolve the photoinitiator. The precursor (Ebecryl 3605) was put in a brown glass beaker, weighed, and then heated to 60° C. for about half an hour until it was totally melted. Crosslinker SR-508, SR-351 and 0.5% (w/w) photoinitiator Irgacure 651 were added into the beaker to mix with the melted precursor by stirring for overnight. To prepare the epoxy resin film on PET slide, the prepared epoxy/acrylate mixture was dropped on the PET slide (75 mm×25 mm) to form a thin film by spin-coating, followed by irradiation for 5 s under UV flood equipment (shuttered UV system, 400 W) in nitrogen atmosphere. The cured epoxy film was subsequently washed by ethanol and DI water for each 3 min to remove any uncured monomer, and then dried under nitrogen flow. Then the epoxy film is ready for fabricating the protein microarray and microfluidic immunoassay device.

Fabrication of Microfluidic Device with UV-Curable Epoxy Resin

Epoxy resin-based microfluidic device was fabricated by the procedure shown in FIG. 2. In detail, SU-8 was used as a photoresist to deposit on a silicon substrate. By using a patterned mask, the SU-8 was developed to a patterned master after photo exposure and was then used to produce PDMS replicas as the molds. The use of the elastic PDMS mold can easily separate the embossed epoxy microstructure and also reduce the fabrication cost due to its high cast fidelity in many molding operations. In more detail, the precursor PDMS, prepared by mixing PDMS elastomer (Sylgard 184 Kit) and curing agent at a ratio of 10:1 (w/w), was poured into the SU-8 master and cured at room temperature for 24 h to produce a replicated PDMS mold. Then, the prepared epoxy/acrylate mixture was poured into the PDMS mold. After it uniformly filled the mold, the epoxy resin thin layercoated PET slide was laminated on top of the mold. A glass slide was placed on the top of the PET film and four clamps were used to secure the whole assembly with certain pressure. The assembly was then UV irradiated for 5 s, followed by removing the elastic PDMS mold from the embossed epoxy microchannels (width×depth×length: 200 μm×100 μm×10 mm) on the PET film. The fabricated microstructure was washed with ethanol and DI water successively. After blow-drying, holes at the inlet and outlet channels were made by drilling. The fabricated structure was covered by the ARFlow® 90128 film, which is clear and possesses dual functionality for bonding components and wicking biological fluids with its hydrophilic coating on one-side, followed by baking at 70° C. for 5 min for complete seal. The hydrophilic properties of the film could reduce the surface tension of fluids for rapid flow of a sample from the inlet area to the reaction sites in this fabricated device. Silicon tubing was employed to connect the inlet with a syringepump for sample delivery and washing. Then, the fabricated multi-channel microfluidic device was used for ELISA conduction.

Fabrication of Protein Microarray on Epoxy Resin Film

The printing buffers with different desired concentrations of the probe protein were prepared and transferred to the 384-well microtiter plate before printing. To optimize the printing buffer, 0.01 M PBS containing different concentrations of glycerol ranging from 0% to 40% and different amounts of triton X-100 ranging from 0% to 0.012% were examined. In other experiments, the optimal printing buffer was employed. Protein loading capacity was characterized by printing Cy3-labeled anti-goat IgG solution with a concentration range from 5 to 1000 μg mL$^{-1}$. Protein microarray was fabricated by contact printing using VersArray Chipwriter™ (Bio Rad, USA) at 60% humidity.

After post-printing incubation, the slides were washed 3 times for each 2 min with TBST (0.01 M TBS with 0.05% Tween 20) to remove unbound probes. Then they were immersed in Blocker™ casein/TBS solution for 1 h to not only quench the unreacted epoxy functional groups on the substrate surface, but also to produce a layer of casein that could reduce the non-specific binding in subsequent steps. For immunoassay, the antigen microarrays were produced with 500 μg mL$^{-1}$ goat IgG in the optimal printing buffer described above. Various concentrations of Cy3-labeled anti-goat IgG (20 μL) from 10 pg mL$^{-1}$ to 10 μg mL$^{-1}$ with 10-fold dilution were used to incubate each array for 1 h at 37° C., followed by washing again (2 min×4 times) with TBST, then bywashing (twice) with DI water for 2 min to remove the detergent and salt, while the diluent was added to another array and regarded as a negative control.

After drying, the microarray was scanned at 543 nm using a laser based microarray scanner (ScanArray GX, PerkinElmer, USA) at a 5-μm resolution. The acquired images were quantitatively analyzed with ScanArray® Express analysis software. The fluorescent intensities were local background-subtracted means for downstream statistical analysis. The acquired data were input to Origin 7.0 for further analysis and plots.

Flow-Through ELISA with Prepared Microfluidic Device

The effect of incubation time on probe immobilization in microchannels was studied by pumping a 10 μg mL$^{-1}$ HRP-labeled anti-goat IgG into the channels and then incubating for different times. After probe immobilization, the unbounded protein was removed by a flow washing process for 3 min. TMB was then pumped in for the enzymatic reaction to yield colors, which were captured by CCD camera. In addition, the peroxidase converted substrates were pumped out into the 384-well ELISA-plates for absorbance measurement (Genios plus, Tecan, USA).

To study the effect of incubation time on antibody-antigen interaction in microchannels, 10 μg mL$^{-1}$ goat IgG was pumped into different channels and incubated for 10 min, followed by blocking with casein for 10 min. Then, the antibody-antigen interaction was conducted in the device by flowing-in 5 μg mL$^{-1}$ HRP-labeled anti goat IgG into different microchannels with different incubation times. The unbounded protein was then removed by a flow washing process for 5 min. TMB was then pumped in for the enzymatic reaction to yield colors for detection. To conduct flow-through sandwich ELISA, the probe antibodies (capture proteins), anti-IL-5 (10 μg mL$^{-1}$) and anti-rabbit IgG (10 μg mL$^{-1}$) antibody were pumped into different microchannels followed by 10 min incubation, the optimal condition identified above in the probe attachment. The same flow-through washing procedure as that used in the study of probe immobilization was performed, while the blocking was performed by pumping in casein for 10 min. The analytes, IL-5 and rabbit IgG diluted in human serum ranging from 10 pg mL$^{-1}$ to 10 μg mL$^{-1}$, were pumped into the fluidic devices and incubated for 10 min, followed by flow through washing with TBS for 4 min. The recognition antibodies, HRP conjugated anti-IL-5 and anti-rabbit IgG antibody for the sandwich detection were then pumped into the channels for a 10 min incubation followed by a 5 min of flow-through washing. Then, the enzyme substrate, TMB, was pumped into the microfluidic channels and converted to product by the captured HRP for colorimetric detection. Additionally, the peroxidase converted product was pumped out into a 384-well plate for absorbance measurement.

Fabrication of Epoxy Resin-Based Protein Microarray

The prepared film was characterized and optimized for protein microarray and microfluidic device fabrication.

UV-Curable Epoxy Resin Film Characterization

Figure 8:
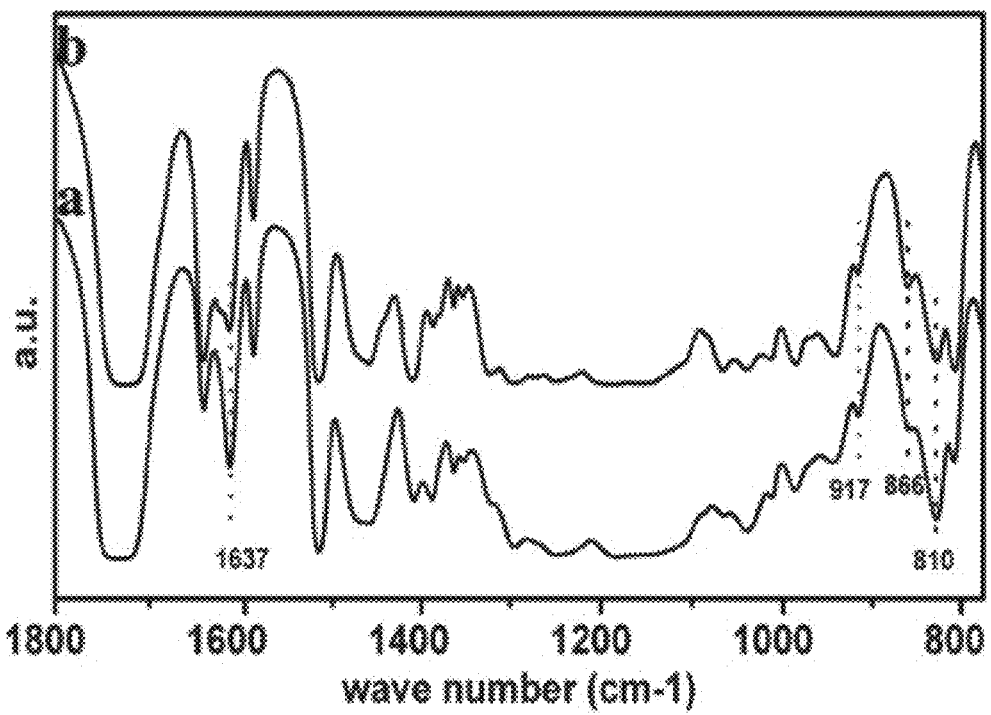
FIG. 8 shows a FTIR spectra of the resin before (a) and after (b) UV exposure.

The prepared epoxy resin and its UV-cured film were characterized by using Attenuated Total Reflection Fourier Transform Infrared (ATR-FTIR) spectroscopy. FIG. 8 shows that the intensity of the characteristic unsaturated double bonds of the acrylate group at 1637 cm$^{-1}$ and 810 cm$^{-1}$ is significantly reduced after UV irradiation, indicating a successful polymerization via acrylate groups. However, the characteristic peaks of epoxide groups including the antisymmetric epoxide ring deformation at 917 cm$^{-1}$, and the symmetric epoxide ring deformation at 866 cm$^{-1}$, can be seen before and after the UV irradiation, showing that the epoxy groups are still intact for protein covalent immobilization after the UV polymerization.

UV-Curable Epoxy Resin Film Optimization

Figure 9:
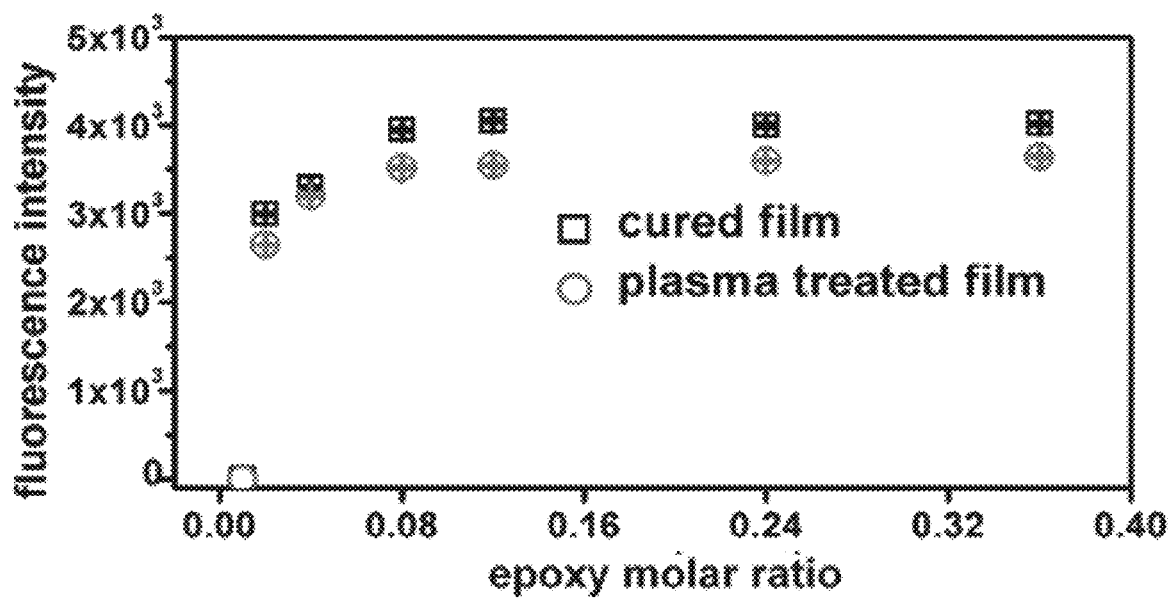
FIG. 9 shows the effect of E/A ratio and hydrophilicity on protein immobilization.

The epoxy density in the resin was controlled by adjusting the epoxy and acrylate molar (E/A) ratio. To obtain an optimal E/A ratio, protein immobilization was conducted by loading of Cy3-labeled anti-goat IgG (500 ng mL$^{-1}$) on different epoxy resin films. The results shown in FIG. 9 illustrate that the samples with an E/A ratio of less than 0.03 have no detectable fluorescent signal, indicating that the immobilized protein is negligible. The detected fluorescent intensity increases steadily with increasing the E/A ratio over a range of 0.03 to 0.08, until the plateau fluorescence intensity is reached at the E/A ratios higher than 0.08 (FIG. 9). To compromise the maximum protein immobilization capability with a low viscosity for non-fragile epoxy films, the optimal E/A molar ratio of the resin is selected as 0.08. Interestingly, the fluorescent intensity does not show significant reduction on plasma treated epoxy resin film (FIG. 9) although its hydrophilicity is remarkably improved (FIG. 9). This may indicate that the protein nonspecific adsorption resulted from the hydrophobic interaction is insignificant, and the covalent binding of the epoxy group with the amino group of the protein is the dominant factor in the protein immobilization.

Protein Immobilization Kinetics on UV-Cured Epoxy Film

Figure 10:
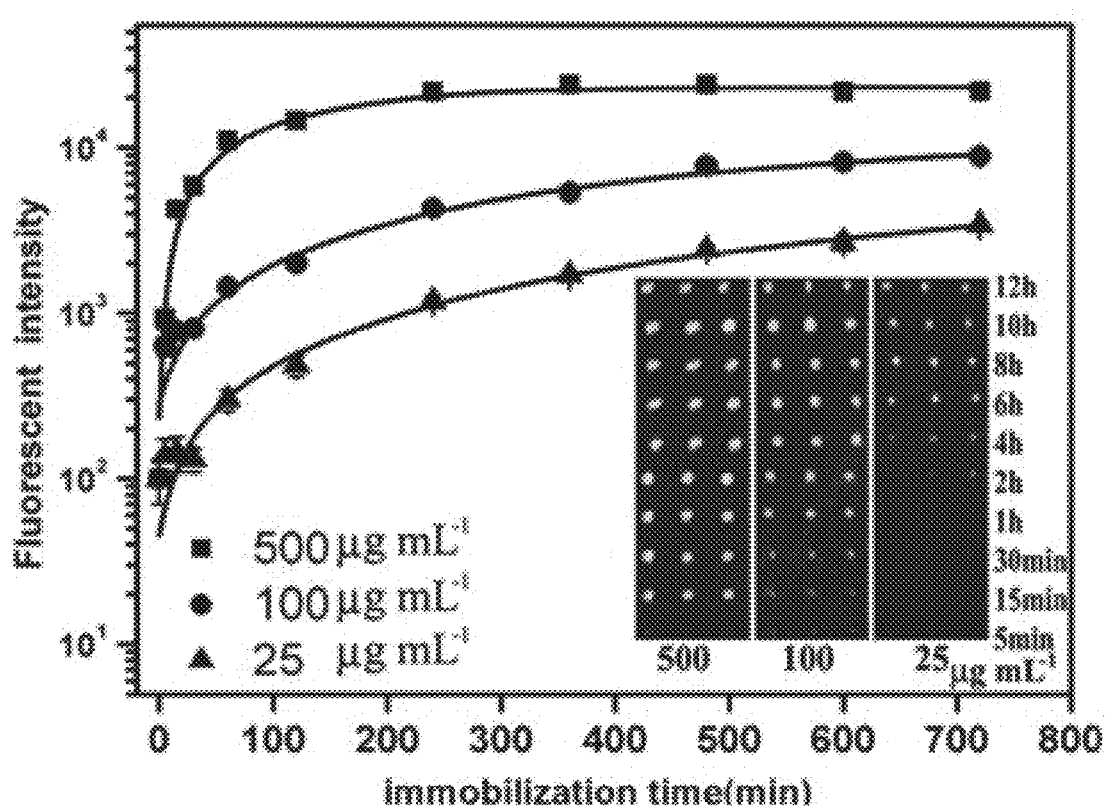
FIG. 10 shows the protein immobilization kinetics on epoxy resin: signal intensity vs. incubation time.

In addition, concentrations of 25, 100 and 500 μg mL$^{-1}$ were chosen to investigate protein immobilization kinetics, since they can represent different stages of the immobilization. The results are shown in FIG. 10, of which the inset is the images of the tested microarrays. The results clearly illustrate that the fluorescent intensity for the 500 μg mL$^{-1}$ protein increases with the immobilization time much faster than that for 25 and 100 μg mL$^{-1}$ protein, and the plateau can be achieved in less than 4 h. However, the protein immobilization for 25 and 100 μg mL$^{-1}$ could not reach its saturation even after 12 h. The protein immobilization kinetics on the epoxy resin surface was studied by using the following equation:

$$R_t = E^*(1-e^{k_s t}) + R_0 \qquad \text{Equation 1}$$

and $$k_s = k[A] + k_d \qquad \text{Equation 2}$$

Where $E^*$, $k_a$, $k_d$, $R_0$, and $A$ are the activation energy, the association rate constant, the dissociation rate constant, the response at t=0 and the adsorption protein concentration in the aqueous solution, respectively. The values of $k_a$, $k_d$, $E^*$, and $R_0$ are determined by fitting the binding curves of fluorescent intensity vs. times for different immobilization concentrations. The fitted $k_a$ and $k_d$ are $1.38 \times 10^{-5}$ M$^{-1}$s$^{-1}$ and $9.82 \times 10^{-6}$ s$^{-1}$, respectively.

Figure 3:
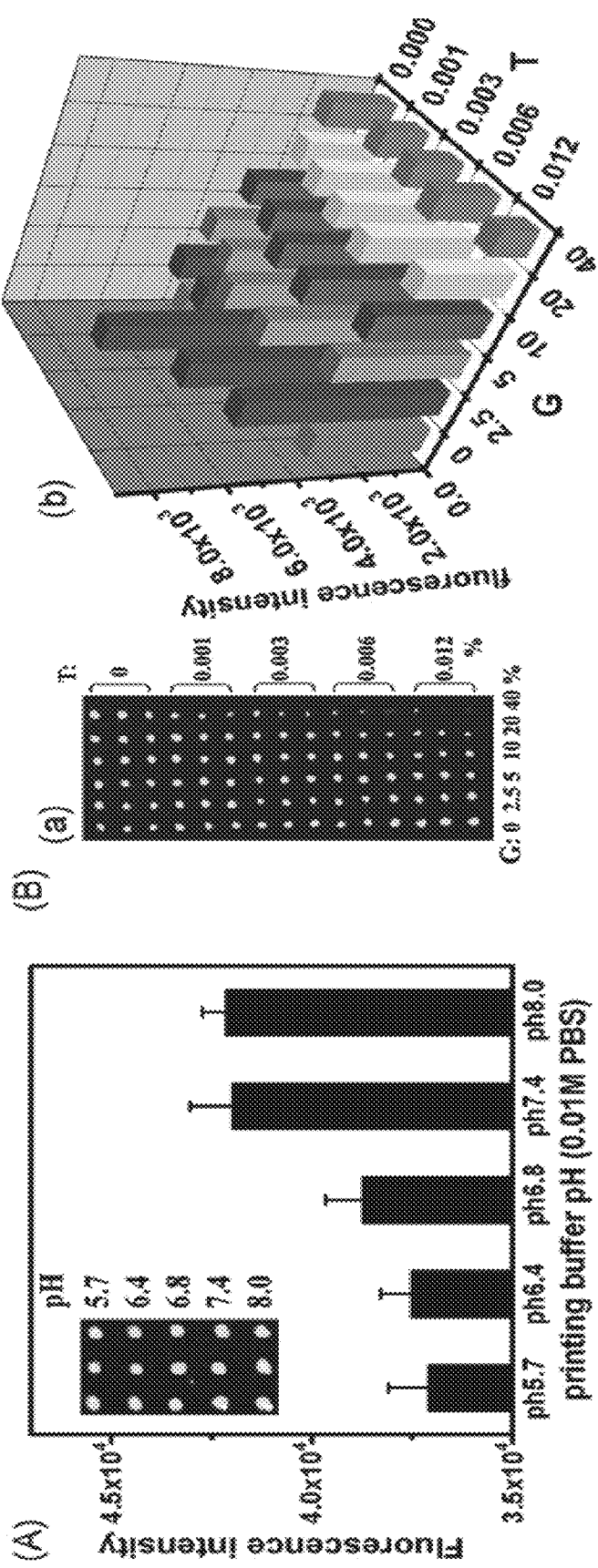
FIG. 3 (A) illustrates the signal intensity vs. printing buffer's pH

The performance of the epoxy resin-based protein microarray could be improved by optimization of printing buffer, probe concentration, and incubation time. The properties of the printing buffer can significantly affect the probe binding capacity and the spots quality. The effect of the printing buffer pH was evaluated by directly spotting Cy3-labeled anti-goat IgG on the epoxy resin films. As shown in FIG. 3(A), the pH 7.4 PBS gives the highest fluorescence signal, indicating the efficient protein immobilization. Thus, a pH 7.4 PBS was used to prepare the printing buffer for other optimization experiments. Glycerol is an additive in the printing buffer to prevent the spotted probe from dehydration and subsequent denaturation, since the nanoliter-droplets could quickly evaporate even at room temperature. Additionally, adding Triton X-100, a non-ionic surfactant, to the printing buffer can increase the homogeneity and diameter of the spots. In our previous work, both additives were used to improve antibody microarray performance; however, they were only effective at a certain threshold concentration, and deviation from this threshold could cause negative effects. A delicately tuned optimization is necessary when using them in the printing buffer. In this work, glycerol concentrations of 2.5%, 5%, 10%, 20%, and 40%, and Triton X-100 concentrations of 0.001%, 0.003%, 0.006%, and 0.012% in the printing solution were examined. The scanned image of the fabricated microarray and the fluorescence intensity vs. the glycerol and triton concentrations are shown in FIG. 3(B) (a) and (b), respectively.

Figure 4:
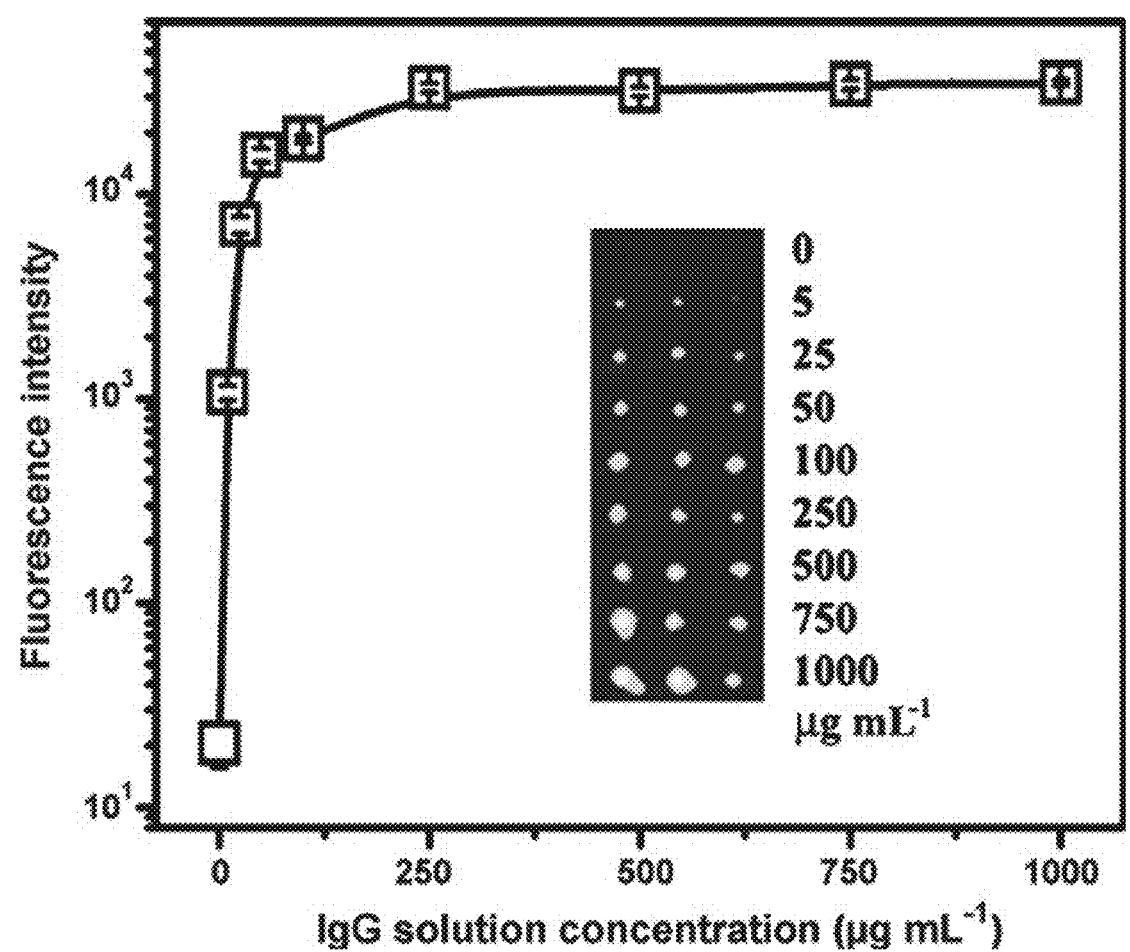
FIG. 4 illustrates protein loading capacity of epoxy resin substrate: signal intensity vs. probe concentrations.

The results reveal that the buffer containing 2.5% glycerol, 0.003% Triton X-100 has the highest signal intensity. Thus, the optimal printing buffer is 0.01M PBS (pH 7.4) containing 2.5% glycerol and 0.003% Triton X-100. The sensitivity of protein microarrays could be greatly influenced by the amount of immobilized probes. Generally, the larger amount of probes is immobilized, the higher sensitivity of the detection microarrays is obtained. However, the amount of immobilized probe does not increase linearly with its concentration in the printing buffer due to the limit of substrate loading capacity. The optimal printing concentration was investigated by spotting different concentrations of Cy3-labeled anti-goat IgG on epoxy resin film. The dependency of fluorescence intensity on the protein concentrations in printing buffer is shown in FIG. 4, illustrating that the intensity sharply increases with the increase of the protein concentration, until a plateau intensity is reached at 250 µg mL$^{-1}$.

Thus, 250 µg mL$^{-1}$ is the optimal probe concentration for both the maximum surface protein immobilization and economic consideration. Theoretically, a higher amount of the capture protein immobilized can result in a larger detection dynamic range when a same method is used to detect the target biomolecule. Thus, the high amount of immobilized IgG on the epoxy-film can be further supported by its larger detection dynamic range in comparison to the reported work based on the same detection method as shown in the latter discussion. The high immobilization capability is very likely ascribed to its inherent highly concentrated epoxides in the epoxy resin. Further, it is not difficult to understand that the epoxide group or other functional groups introduced by multiple surface reactions are less introduced because of their possible poor yield from the multiple reactions. In addition, the protein immobilization kinetics was also investigated for optimization of protein immobilization time (see supplementary materials). These results demonstrate that the probe concentration and the immobilization time have significant effects on the immobilization efficiency.

Protein Analysis with Epoxy Resin-Based Protein Microarray

Figure 5:
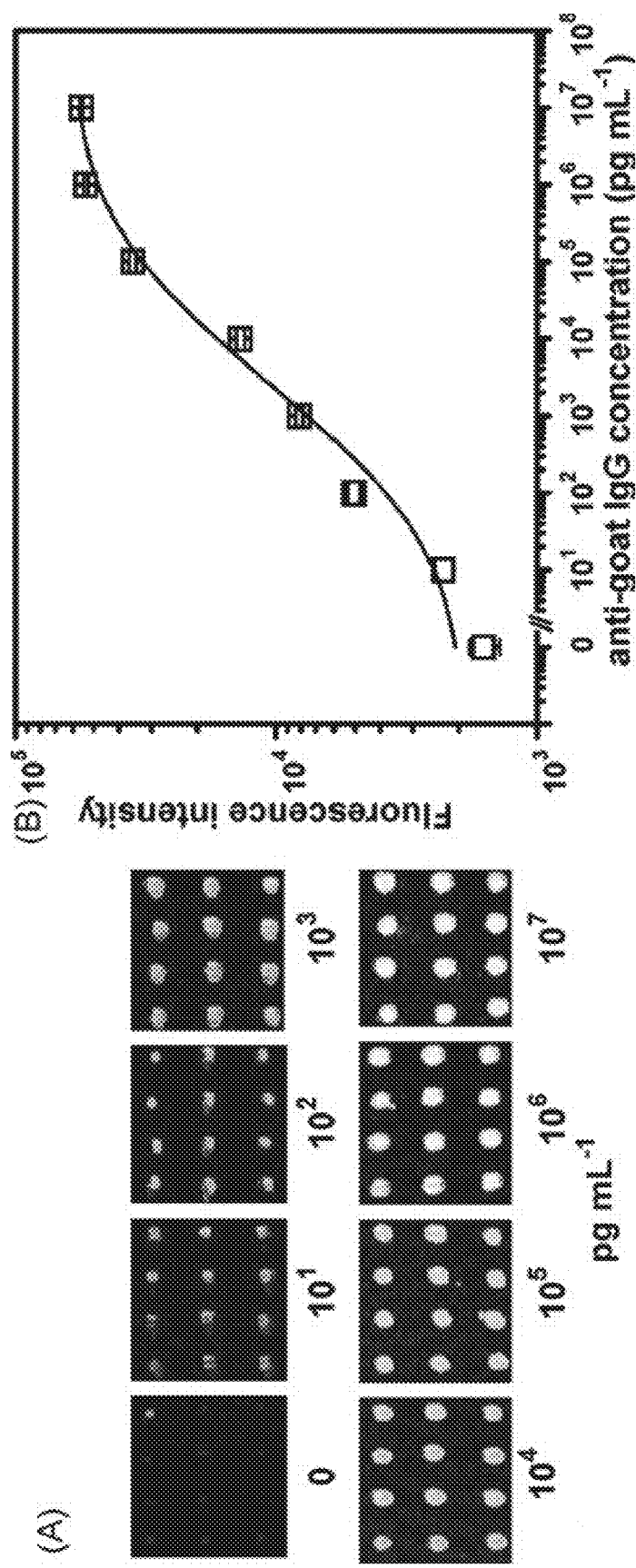
FIG. 5(A) shows a fluorescent image of microarray and FIG. 5(B) shows the dose dependent curve of UV-curable epoxy resin-based protein microarray for detection of anti-goat IgG.

The dynamic range and LOD of protein microarrays fabricated on the epoxy resin film were characterized by using direct immunoassay with goat IgG and anti-goat IgG as model proteins. 500 µg mL$^{-1}$ goat IgG in the optimal printing buffer discussed above was contact printed on the epoxy film for immunoassay microarrays. Various concentrations of anti-goat IgG (Cy3 label) from 10 pgmL$^{-1}$ to 10 µg mL$^{-1}$ with 10-fold dilution were used to incubate each array. FIG. 5(A) illustrates that the fluorescence intensity rises with the increase of analyte concentration. The fluorescence intensity of each spots was quantitatively analyzed with ScanArray® Express analysis software, and a plot of fluorescence intensity vs. concentrations of the analyte (anti-goat IgG) was obtained by using Origin 7.0. FIG. 5(B) shows the calibration curve of anti-goat IgG over a concentration range of 10 pg mL$^{-1}$ to 10 µg mL$^{-1}$. A sigmoid curve ($R_2$=0.989) can be seen over the whole detected concentration range, showing a linear range (the concentration range that gave the best fit to the linear equation y=mx+b) from 10 to 1×10$^6$ pg mL$^{-1}$ on the cured epoxy film. It indicates that the dynamic range is from 10 to 1×10$^6$ pg mL$^{-1}$. LOD is determined as three standard deviations above the background and is about 10 pg mL$^{-1}$. The dynamic range and LOD are two important parameters to characterize the performance of protein microarray. In comparison to the reported direct immunoassay works for detection of IgG, in which the LOD of 150 pg mL$^{-1}$ and detection dynamic range of 4 orders of magnitude on carboxyl terminated dendrimer-coated surface, and the detection dynamic range of 50 to 200 ng mL$^{-1}$ on 3D micro/nano porous silicon structures are demonstrated, respectively, the epoxy resin-based protein array exhibits very comparable LOD and larger dynamic range. It is also a simple approach due to the inherent functional epoxide group in the epoxy resin for directly binding proteins without the additional multiple surface reactions for preactivation. In our early work, the sandwich immunoassay conducted with a multi-step surface epoxide-functionalized PET (PGMA-PET) substrate-based protein array shows a LOD of 10 pg mL$^{-1}$ and a dynamic range of five orders of magnitude. Although the work here uses the direct immunoassay to detect IgG and may not be proper for direct performance comparison, it achieves the identical performance while does not need the multi-step functionalization as in our previous work.

Optimization of Flow-Through ELISA in Epoxy Resin-Based Microfluidic Device

Figure 6:
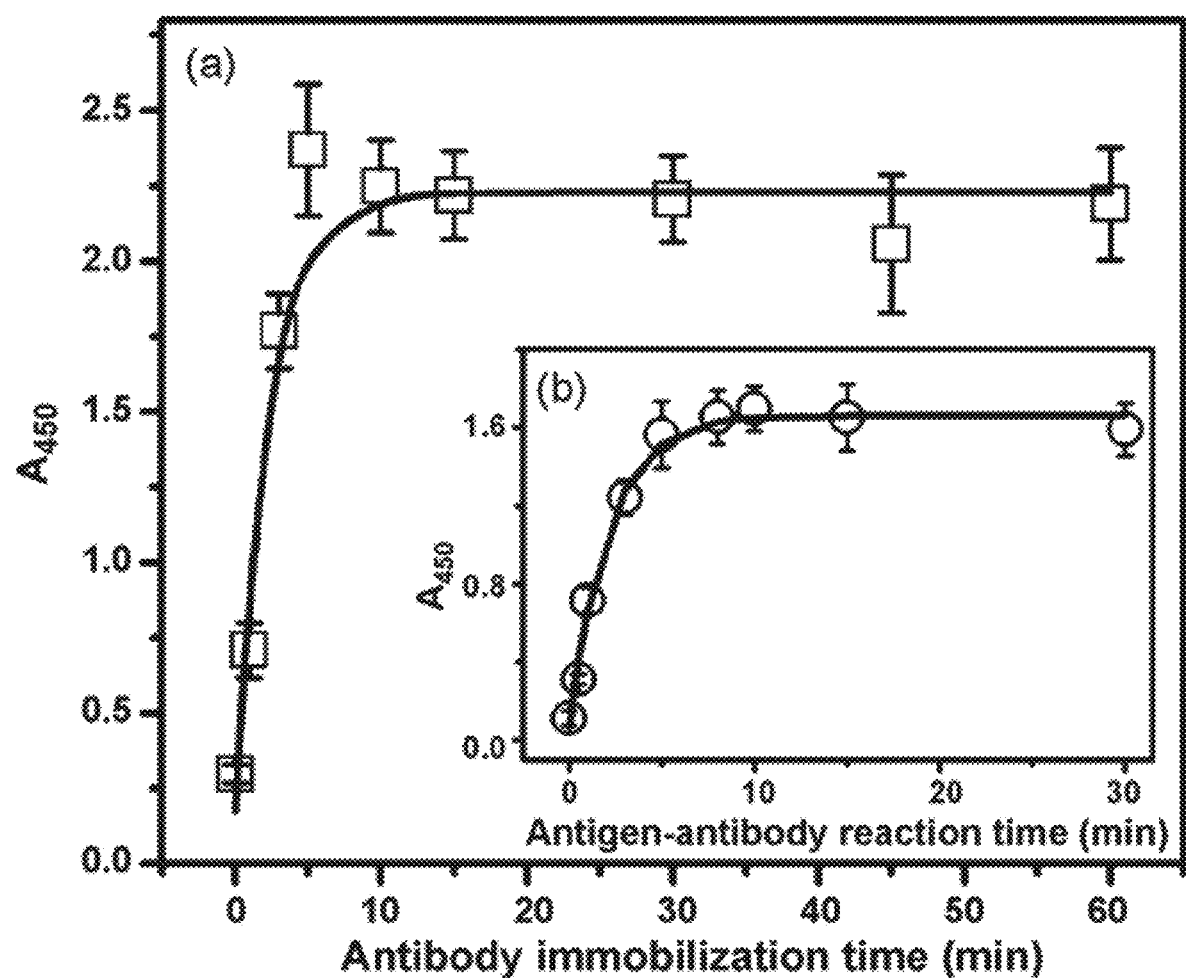
FIG. 6 shows the absorbance signal at different antibody immobilization times. Insert figure: absorbance signal at different antigen-antibody interaction time.

Epoxy resin-based microfluidic devices were fabricated to explore its application in simultaneous multiple flow-through detection of proteins. The protein immobilization and detections including incubation and washing steps were conducted with a flow-through operation in the device. The effects of incubation time on protein immobilization in the microchannels were investigated. The absorbance results in FIG. 6(a) show that the highest signal is obtained after 5 min incubation for protein immobilization. The effect of incubation time on antibody-antigen interaction in the channels is shown in FIG. 6(b), of which the absorbance of peroxidase converted TMB produced in the microchannel reaches a plateau after 10 min incubation. Thus, the optimal protein immobilization time and the efficient antibody-antigen interaction time are 5 and 10 min, respectively.

Flow-Through ELISA for Multiple Detections of Proteins

Figure 7:
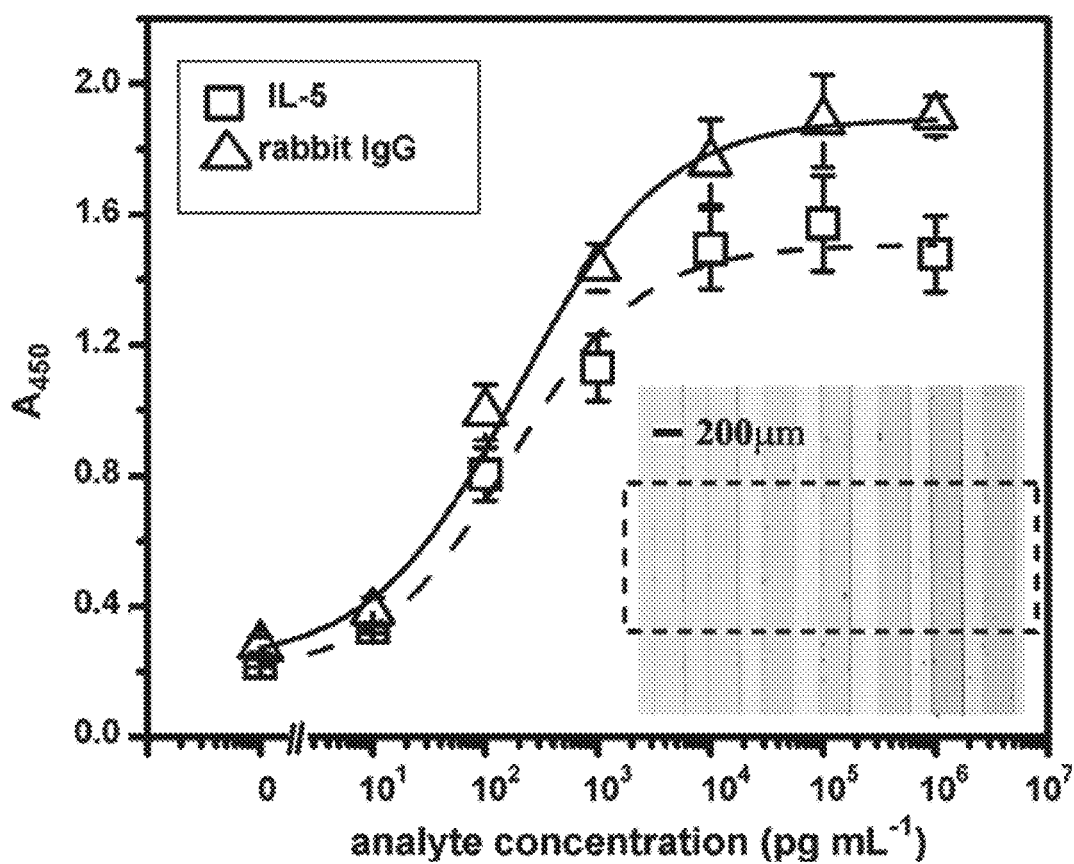
FIG. 7 shows a calibration curve for detection of IL-5 (□) and rabbit IgG (Δ) in epoxy resin-based microchannel. Insert image: flow-through ELISA in microchannels (the channel width is 200 μm), from left to right, the IL-5 concentrations are 0, 10, 100 pg mL$^{-1}$, 1, 10, 100 ng mL$^{-1}$, and 1 μg mL$^{-1}$.

Detection of IL-5 and IgG was conducted in the epoxy resin based microfluidic devices. FIG. 7 shows the calibration curves of IL-5 (□) and rabbit IgG (Δ) over a concentration range of 10 pg mL$^{-1}$ to 10 µg mL$^{-1}$. The experiments were repeated 3 times and the standard deviations calculated by Original 7.0. The sigmoid curves over the concentration range have $R_2$ of 0.994 and 0.997 for detection of IL-5 and rabbit IgG, respectively, as in FIG. 7. The calibration curves show a typical immunoassay characteristics with a linear range over 1×10$^2$ to 1×10$^4$ pg mL$^{-1}$ for detection of both IL-5 and rabbit IgG.

The LOD is set to be three times higher than the standard deviations of the signals at background (no analytes in the microchannel). Therefore, the LODs of our device for IL-5 and rabbit IgG are ca. 100 pg mL$^{-1}$. Moreover, the epoxy resin-based microfluidic device can be used for simple colorimetric detection as shown in the inset of FIG. 7 (IL-5 detection image), in which no color is observed from the channels of background (no analytes) and 10 pg mL$^{-1}$ IL-5. Blue colors can be observed clearly from the channels with the concentrations of IL-5 equal to or higher than 100 pg mL$^{-1}$. It is still very comparable with that of the poly(methyl methacrylate) (PMMA) microfluidic devices with enzyme (HRP) converted fluorescent signal. Since the color changes for the protein detection can be directly observed by the naked human eye, the microfluidic device demonstrates a great potential for fabricating a portable, flow through, detection equipment-free device for screening diseases by immunoassay. The microdevice could also be fabricated using a web to web embossing manufacturing process developed in our previous work for mass production.

In brief, a new and economic approach to fabricate protein microarray and microfluidic immunoassay device with a UV curable epoxy resin was investigated. The microarray showed an extremely low standard deviation error, a broad dynamic range of 5 orders of magnitude, and a LOD of 10 pg mL$^{-1}$. More promisingly, the ELISA microfluidic device also possesses a LOD of 100 pg mL$^{-1}$ and a dynamic range of 4 orders of magnitude in serum sample, which is better or at least comparable to that measured in PBS with the microfluidic devices made by more complicated fabrication processes. The present invention also demonstrates the feasibility of a microfluidic device for colorimetric immunoassays that can be detected with the naked human eye, then providing potential to fabricate portable immunoassay devices for health point of care and infectious diseases screening. It is worthy of a note that it is possible to make a complete epoxy microfluidic device with the epoxy resins used in the present invention by molding, which could be more cost effective and easy to fabricate the sensors.

The invention claimed is:

1. A method of manufacturing a micro patterned device, wherein the method comprises:
   providing a mold;
   applying a light curable epoxy resin to the mold to obtain a light curable epoxy resin filled mold;
   providing a polymeric film;
   coating the polymeric film on one side with a layer of the light curable epoxy resin, wherein the polymeric film is transparent to radiation by light;
   irradiating with light the layer of the light curable epoxy resin coated onto the polymeric film to cure the epoxy resin and to provide a cured epoxy resin-coated polymeric film;
   applying the cured epoxy resin-coated polymeric film with the coated-side over the light curable resin filled mold; and
   irradiating with light the light curable resin filled mold, to which the cured epoxy resin-coated polymeric film is applied, to cure the epoxy resin in the mold, wherein the cured epoxy resin forms the micro patterned device.

2. The method of claim 1, further comprising, prior to applying the light curable epoxy resin to the mold, dissolving the light curable epoxy resin in a mixture that includes a photoinitiator.

3. The method of claim 2, wherein the mixture comprises at least one solvent.

4. The method of claim 3, wherein the solvent is an acrylate.

5. The method of claim 4, wherein the acrylate is selected from the group consisting of diacrylates, triacrylates, tetraacrylates and mixtures thereof.

6. The method of claim 4, wherein the acrylate is selected from the group consisting of dipropylene glycol and trimethylolpropane triacrylate, and mixtures thereof.

7. The method of claim 2, wherein the photoinitiator is selected from the group consisting of benzophenone, benzophenone/1-hydroxycyclohexylphenyl-ketone (1/1 ratio), 2,2-dimethoxy-2-phenylacetophenone (DMPA, Irgacure 651), 2-hydroxy-2-methyl-1-phenylpropanone, 1-hydroxycyclohexylphenyl-ketone, 2,4,6-trimethylbenzoyl diphenyl phosphine oxide, isopropyl thioxanthone (2- and 4-isomer mixture), 2-methyl-1-[4-(methylthio)phenyl]-2-morpholino-propan-1-one, 2-ethylhexyl-4-(dimethylamino)benzoate, ethyl-4-(dimethylamino)benzoate, acrylated benzophenone derivative, benzophenone derivative, acrylated amine synergist, copolymerizable amine synergist, acrylated amine synergist, and methyldiethanolamine.

8. The method of claim 2, wherein the photoinitiator is present in the mixture in an amount of between about 0.2% to about 2% (w/w).

9. The method of claim 1, wherein applying the cured epoxy resin-coated polymeric film comprises laminating the cured epoxy resin-coated polymeric film over the light curable resin filled mold.

10. The method of claim 1, wherein the light curable epoxy resin is a UV curable epoxy resin.

11. The method of claim 1, wherein the light curable epoxy resin is a UV curable epoxy acrylate.

12. The method of claim 11, wherein the epoxy acrylate is acrylated bisphenol-A epoxy resins or diacrylate esters of bishphenol derivatives.

13. The method of claim 1, wherein coating the polymeric film with the layer of the light curable resin comprises spin-coating the layer of the light curable resin.

14. The method of claim 1, wherein the mold and/or the polymeric film is made of a material selected from the group consisting of poly(methyl methacrylate) (PMMA), acetonitrile-butadiene-styrene (ABS), polyethylene terephthalate (PET), poly-(dimethylsiloxane) (PDMS), polycarbonate, polyethylene, polystyrene, polyolefin, polypropylene, polyimide, and a polymeric organosilicon.

15. The method of claim 14, wherein the polymeric organosilicon is poly(dimethyl siloxane) (PDMS) or poly(methyl hydrosiloxane) (PMHS).

16. The method of claim 1, further comprising removing the cured epoxy resin from the mold after irradiation.

* * * * *